(12) United States Patent
Lee (10) Patent No.: US 6,551,591 B1
(45) Date of Patent: Apr. 22, 2003

(54) ANTIBIOTICS FROM MICROBISPORA

(75) Inventor: May D. Lee, Los Altos, CA (US)

(73) Assignee: Essential Therapeutics, Inc., Mountain View, CA (US)

( * ) Notice: Subject to any disclaimer, the term of this patent is extended or adjusted under 35 U.S.C. 154(b) by 0 days.

(21) Appl. No.: 09/949,230

(22) Filed: Sep. 7, 2001

(51) Int. Cl.$^7$ .................. A01K 35/00; C12P 21/02; C12P 21/04
(52) U.S. Cl. ............... 424/115; 435/71.3; 435/252.1
(58) Field of Search ................... 424/115, 118; 435/71.3

(56) References Cited

U.S. PATENT DOCUMENTS

| | | | |
|---|---|---|---|
| 5,312,738 A | 5/1994 | Hamill et al. | 435/75 |
| 5,378,463 A | 1/1995 | Schroeder et al. | 424/121 |
| 5,484,717 A | 1/1996 | Zaccardi | 435/119 |
| 6,187,568 B1 | 2/2001 | Nishida et al. | 435/119 |

OTHER PUBLICATIONS

Argoudelis, et al, "Argoudelis, Application of", (Cust & Pat. App. 19700 434 F.2d 1390.

Lee, Ving J., et al., "Efflux–Mediated Resistance to Antibiotics in Bacteria: Challenges and Opportunities", *Current literature: Antibacterial Research*, vol. 2, No. 2, 1998, pp. 39–42.

Aoyagi, T., et al. "Benastatins A and B. New Inhibitors of Glutathione S–Transferase, Produced by Streptomyces so. MI384–DF12", *The Journal of Antibiotics*, vol. 45, No. 9, Sep. 1992, pp. 1385–1396.

Li, Xian–Zhi, et al., "Role of Efflux Pump(s) in Intrinsic Resistance of *Psedomonas aeruginosa*: Resistance to Tetracycline, Chloramphenicol, and Norfloxacin", *Antimicrobial Agents and Chemotherapy*, vol. 38, No. 8, Aug. 1994, p. 1732–1741.

Sahl, H., et al., "Lantibiotics: Biosynthesis and Biological Activities of Uniquely Modified Peptides from Gram–Positive Bacteria", *Annual Reviews*, 1998, 52:41–79.

*Primary Examiner*—Herbert J. Lilling
(74) *Attorney, Agent, or Firm*—Bernard F. Rose; Bingham McCutchen LLP (57) ABSTRACT

The present invention provides a novel strain of *Microbispora corallina*, means for identifying it, methods for culturing it at several different levels, two new antibiotics derived from the cultures and the physico-chemical characteristics of those compounds and their biological activity against a variety of microorganisms.

10 Claims, 7 Drawing Sheets

ANTIBIOTICS FROM MICROBISPORA

FIELD OF THE INVENTION

This invention relates to the fields of chemistry, bacteriology, biology, biochemistry, pharmacology and medicine. In particular it relates to two new antibiotics isolated from a fermentation broth of a novel strain of *Microbispora corallina*.

BACKGROUND OF INVENTION

Over the past 60 years, a broad range of antibiotics, have become available for the treatment and prevention of bacterially transmitted disease. Penicillin, streptomycin, aureomycin, cephalosporin, bacitracin, erythromycin, novobiocin, methicillin, neomycin, chloramphenicol, kanamycin, chlortetracycline,to name a few—each of these drugs, isolated from microorganisms, has provided a great benefit to the well-being of people and animals the world around. Unfortunately, the widespread use of antibiotics, combined with the natural proclivity of target organisms to find a way to survive such attack, has resulted in an alarming increase in the number of resistant bacterial strains. This roster of resistant species includes a number of clinically important bacteria such as Staphylococcus, Salmonella, Enterobacteriaceae and Pseudomonas, in particular, the species *S. aureus* and *S. pneumoniae*. Thus, there continues to be an urgent need for new drugs, exhibiting novel modes of action unrecognized by target organisms, to overcome the resistance of these and other species of bacteria.

While a great deal of effort is being expended to design new, partially or entirely synthetic drugs to fill the voids in therapeutic efficacy created by the emergence of resistance, nature continues to be a invaluable source of such compounds.

SUMMARY OF THE INVENTION

Thus, the present invention relates to two antibiotics designated MF-BA-1768$\alpha_1$ and MF-BA-1768$\beta_1$, to their production by fermentation, to methods for their recovery and concentration from fermentation broth, and to processes for their purification. It includes within its scope the antibiotics in dilute form, in crude concentrates, in complexes of various or all components, and in pure form as individual compounds. The present invention also includes a novel strain of *Microbispora corallina*, which produces the compounds. The strain is identified by the DNA sequence that codes for its partial 16S rRNA sequence and by its nutrient utilization pattern. The chemical structures of the new antibiotics are presently unknown but four potential structural features have been deduced based on partial 2-D NMR data including $^1H$—$^1H$ correlation (COSY) and $^1H$—$^{13}C$ correlation (HMQC). The compounds are characterized by their physical and chemical properties including UV, IR, and $^1H$ NMR spectra. Their molecular weights were determined by ESI-FTMS.

In one aspect, this invention relates to antibiotic MF-BA-1768$\alpha_1$, or a pharmaceutically acceptable salt thereof, having the physicochemical characteristics, in the non-salt form, described in detail below.

In another aspect, this invention relates to antibiotic MF-BA-1768$\beta_1$, or a pharmaceutically acceptable salt thereof, having the physicochemical characteristics, in the non-salt form, described in detail below.

In a further aspect, this invention relates to a process for producing antibiotic MF-BA-1768$\alpha_1$, comprising cultivating a strain of *Microbispora corallina*, NRRL 30420, or an antibiotic MF-BA-1768$\alpha_1$-producing mutant, variant or recombinant form thereof, in a culture medium containing assimilable sources of carbon, nitrogen and inorganic salts under aerobic fermentation conditions until antibiotic MF-BA-1768$\alpha_1$, is produced and then recovering the antibiotic therefrom.

In a still further aspect, this invention relates to a process for producing antibiotic MF-BA-1768$\beta_1$, comprising cultivating a strain of *Microbispora corallina*, NRRL 30420, or an antibiotic MF-BA-1768$\beta_1$-producing mutant, variant or recombinant form thereof, in a culture medium containing assimilable sources of carbon, nitrogen and inorganic salts under aerobic fermentation conditions until antibiotic MF-BA-1768$\beta_1$, is produced and then recovering the antibiotic therefrom.

An aspect of this invention is a biologically pure culture of *Microbispora corallina*, NRRL 30420, or an antibiotic MF-BA-1768$\alpha_1$-producing mutant, variant or recombinant form thereof.

An aspect of this invention is a biologically pure culture of *Microbispora corallina*, NRRL 30420, or an antibiotic MF-BA-1768$\beta_1$-producing mutant, variant or recombinant form thereof.

A bacterial strain comprising DNA SEQ. No. 1, or a sequence having at least 80% homology therewith, is an aspect of this invention.

An aspect of this invention is a pharmaceutical composition comprising a therapeutically effective amount of compound MF-BA-1768$\alpha_1$ and a pharmaceutically acceptable carrier, wherein compound MF-BA-1768$\alpha_1$ has the physicochemical characteristics described in detail below.

An aspect of this invention is a pharmaceutical composition comprising a therapeutically effective amount of compound MF-BA-1768$\beta_1$ and a pharmaceutically acceptable carrier, wherein compound MF-BA-1768$\beta_1$ has the physicochemical characteristics described in detail below.

An aspect of this invention is a method for treating a bacterial infection comprising administering to a patient in need thereof a therapeutically effective amount of compound MF-BA-1768$\beta_1$, which has the physicochemical characteristics described in detail below.

An aspect of this invention is a method for treating a bacterial infection comprising administering to a patient in need thereof a therapeutically effective amount of compound MF-BA-1768$\beta_1$, which has the physicochemical characteristics described in detail below.

A further aspect of this invention is either of the preceding two methods wherein the infection-causing bacteria are from the genera Staphylococcus, Enterococcus, Streptococcus, Haemophilus or Escherichia.

An aspect of this invention is the above methods wherein the infection-causing bacteria are *Staphylococcus aureus, Staphylococcus epidermis, Staphlyococcus haemolyticus, Enterococcus faecalis, Enterococcus faecium, Streptococcus pneumoniae, Streptococcus pyrogenes, Haemophilus influenzae* or *Eschericia coli*.

DETAILED DESCRIPTION OF THE INVENTION

Brief Description of the Tables

Table 1 is a list of the cultural characteristics of *Microbispora corallina* strains MF-BA-1768, JCM 12066, and JCM 12067.

Table 2 is a carbon source utilization listing for *Microbispora corallina* strains MF-BA-1768, JCM 12066, and JCM 12067

DEFINITIONS

As used herein, the term "method" refers to manners, means, techniques and procedures for accomplishing a given task including, but not limited to, those manners, means, techniques and procedures either known to, or readily developed from those manners, means, techniques and procedures known to practitioners of the chemical, pharmaceutical, biological, biochemical and medical arts.

As used herein, a "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

A "pharmaceutically acceptable salt" of a compound of this invention refers to the compound in a charged form, either a cation or an anion, along with a counter-ion. When the compound of this invention is in a negatively charged form, that is, it is anionic, the positively charged counter ion may be for example, without limitation, sodium, potassium, lithium, magnesium, calcium, zinc, aluminum or ammonium. When the compound of this invention is in a positively charged form, the negatively charged counter ion may be for example, without limitation, chloride, bromide, iodide, nitrate, phosphate, sulfate, acetate, propionate, butyrate, maleate, fumarate, methanesulfonate, ethanesulfonate, 2-hydroxyethylsulfonate, n-propylsulfonate isopropylsulfonate, lactate, malate or citrate. Pharmaceutically acceptable salts may be obtained by reacting a compound of the invention with an organic or inorganic base, such as benzathene, chloroprocaine, choline, diethanolamine, ethylenediamine, meglumine, procain, and the hydroxide, alkoxide, carbonate, bicarbonate, sulfate, bisulfate, amide, alkylamide, or dialkylamide salts of the following metal cations.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, a "bacterial infection" refers to the establishment of a sufficient population of pathogenic bacteria in a patient to have a deleterious effect on the health and well-being of the patient and/or to give rise to discernable physiological symptoms associated with the particular bacteria.

As used herein, the terms "treat", "treating" or "treatment" refers to a method of alleviating or abrogating a bacterial infection and/or its attendant symptoms.

As used herein, "administer," administering," or "administration" refers to the delivery of a compound, or salt thereof, of the present invention or of a pharmaceutical composition containing a compound or salt of this invention to a patient for the purpose of treating or preventing a bacterial infection.

The term "patient" refers to any living entity capable of being infected by bacteria. In particular, a "patient" refers to a mammal such as a dog, cat, horse, cow, pig, rabbit, goat or sheep. Most particularly, a patient herein refers to a human being.

The term "therapeutically effective amount" as used herein refers to that amount of the compound being administered which will relieve to some extent one or more of the symptoms of the bacterial infection being treated. That is, a therapeutically effective amount refers to that amount of a compound of this invention that has the effect of (1) reducing, preferably eliminating, a population of bacteria in a patient's body, (2) slowing to some extent, preferably stopping, proliferation of bacteria in a patient's body, (3) slowing to some extent, preferably stopping, spread of the infection caused by the bacteria or (4) relieving to some extent, preferably, eliminating, one or more symptoms associated with the particular bacterial infection.

DISCUSSION

Actinomycetale Strain MF-BA-1768

Compounds MF-BA-1768$\alpha_1$ and MF-BA-1768$\beta_1$ were formed during the cultivation of a new strain of Actinomycetaceae. The microorganism is maintained in the culture collection of Microcide Pharmaceuticals, Inc., Mountain View, Calif. as culture number MF-BA-1768. A viable culture of this microorganism was deposited on Mar. 8, 2001, under the provisions of the Budapest Treaty with the Patent Culture Collection Laboratory, Northern Regional Research Center, U.S. Department of Agriculture, Peoria, Ill. 61604, and has been added to its permanent collection. It has been assigned strain designation NRRL 30420.

The microorganism giving rise to culture MF-BA-1768 was isolated from soil roots of *Arachis hipogea* collected in Majalengka, West Java, Indonesia. The DNA sequence which codes for the partial 16S rRNA sequence of MF-BA-1768, was determined to be the following:

5'-1 AGGCTGGATC ACCTCCTTTC TAGCTGGATG
    AGTTTGATCC TGGCTCAGGC TGGATCACCT
61  CCTTTCTAGC TGGATGAGTT TGATCCTGGC
    TCAGGACGAA CGCTGGCGGC GTGCTTAACA
121 CATGCAAGTC GAGCGGAAAG GCCCTTCGGG
    GTACTCGAGC GGCGAACGGG GAGTAACAC
181 GTGAGTAACC TGCCCCTGAC TCTGGGATAA
    GCCTGGGAAA CCGGGTCTAA TACCGGATAT
241 GACACATGGT CGCATGAGCG GTGTGTGGAA
    AGTTTTTTCG GTTGGGGATG GGCTCGCGGC

```
301  CTATCAGCTT GTTGGTGGGG TGATGGCCTA
     CCAAGGCGAC GACGGGTAGC CGGCCTGAGA
361  GGGCGACCGG CCACACTGGG ACTGAGACAC
     GGCCCAGACT CCTACGGGAG CAGCAGTGG
421  GGAATATTGC GCAATGGGCG GAAGCCTGAC
     GCAGCGACGC CGCGTGGGGG TGACGGCCT
```

Based on the partial 16S rRNA sequence, culture MF-BA-1768 is considered to be a new strain of *Microbispora corallina* closely related to *M. corallina* JCM 10266, and JCM 10267. Culture MF-BA-1768 has the cultural, macro-morphological and physiological characteristics shown in Tables 1 and 2, below.

TABLE 1

Culture Characteristics of *Microbispora corallina* strains MF-BA-1768, JCM 12066, and JCM 12067

| Growth Medium | MF-BA-1768 | | | JCM 12066 | | | JCM 12067 | | |
|---|---|---|---|---|---|---|---|---|---|
| | Growth[a] | Obverse Color | Reverse Color | Growth[a] | Obverse Color | Reverse Color | Growth[a] | Obverse Color | Reverse Color |
| Bennett's | + | Pink | Buff | + | Pink | Buff | + | Pink | Buff |
| Tyrosine | + | Pinkish-white | Dark tan | + | Off-white | Tan | + | Off-white | Tan |
| Peptone-iron | − | n.a.[b] | n.a.[b] | ± | Pink | Buff | ± | Pink | Buff |
| Casein-starch | + | Pink | Tan | + | Pink | Buff | + | Pink | Buff |
| Czapek-Sucrose | + | Pink | Buff | + | Pink | Buff | + | Pink | Buff |
| Maltose-Tryptone | + | Pink | Buff | + | Pink | Tan | + | Pink | Tan |

[a]+ = growth,
± = light to very light growth,
− = no growth
[b]= not applicable

```
481  TCGGGTTGTA AACCTCTTTC AGCAGGGACG
     AAGTTGACGT GTACCTGTAG AAGAAGCGCC
541  GGCTAACTAC GGTGCCAGCA GCCGCGGTAA
     TACGTAGGGC GCAAGCGTTG TCCGGAATTA
601  TTGGGCGTAA AGAGCTCGTA GGTGGCTTGT
     TGCGTCTGCC GTGAAAGCCC GTGGCTTAAC
661  TACGGGTCTG CGGGTGAATA CGGGCAGGCT
     AGAGGCTGGT AGGGCAAGCG AATTCCTGG
721  TGTAGCGGTT AAATGCGCAG ATATCAGGAG
     GAACACCGGT GCGAAGGCGG CTTGCTGGCC
781  AGTTCTGACG CTGAGGAGCG AAAGCGTGGG
     GAGCGAACAG GATTAGATAC CCTGGTAGTC
841  CACGCTGTAA ACGTTGGGCG CTAGGTGTGG
     GGGTCTTCCA CGATTCCTGT GCCGTAGCTA
901  ACGCATTAAG CGCCCCGCCT GGGGAGTACG
     GCCGCAAGGC TAAAACTCAA AGGAATTGAC
961  GGGGGCCCGC ACAAGCGGCG GAGCATGTTG
     CTTAATTCGA CGCAACGCGA AGAACCTTAC
1021 CAAGGTTTGA CATACACCGG AAAGCTCTGG
     AGACAGAGCC CTCCTTTGGA CTGGTGTACA
1081 GGTGGTGCAT GGCTGTCGTC AGCTCGTGTC
     GTGAGATGTT GGGTTAAGTC CCGCAACGAG
1141 CGCAACCCTT GTTCCATGTT GCCAGCACGC
     CTTCGGGTGG TGGGGACTCA TGGGAGACTG
1201 CCGGGGTCAA CTCGGAGGAA GGTGGGGATG
     ACGTCAAGTC ATCATGCCCC TTATGTCTTG
1261 GGCTGCAAAC ATGCTACAAT GGTCGGTACA
     GAGGGTTGCG ATGCCGTGAG TGGAGCGAA
1321 TCCYWAAAAG CCGGTCTCAG TTCGGATTGG
     GGTCNTGCAA CTCKRMMMCC ATGAAAGTCG
1381 GAGTCGCNTM GTAATCGCAG ATCAGCAACG
     CTTGCGGTGA ATACGTTNCC GGGCCTTTGT
1441 ACACACCGGC CCGTCACGTT ACGAAAAGTC
     GGCAACACCC CGAAAGCCCG TNGGCCAACC
1501 ACTTTTGGGG GGAACCGTCC AAAGGTGGGG
     CTTGGCAATT GGGACNAAAT CNTAACAAGG
1561 TAACCCTNCC CGGAAGGTCC GGTTGGNTC-3'
```

TABLE 2

Carbon Source Utilization of *Microbispora corallina* stains MF-BA-1768, JCM 12066, and JCM 12067

| | Growth[a] | | |
|---|---|---|---|
| Carbon Source | MF-BA-1768 | JCM 12066 | JCM 12067 |
| Basal medium (no carbon source) | − | − | − |
| D-glucose | ± | + | + |
| D-fructose | ± | + | + |
| Rhamnose | ± | + | + |
| I-inositol | − | + | + |
| D-xylose | + | + | + |
| Sucrose | − | + | + |
| D-mannitol | ± | + | + |
| Raffinose | ± | ± | ± |

[a]+ = growth, ± = light to very light growth, − = no growth

Structural Features

Figure 5:
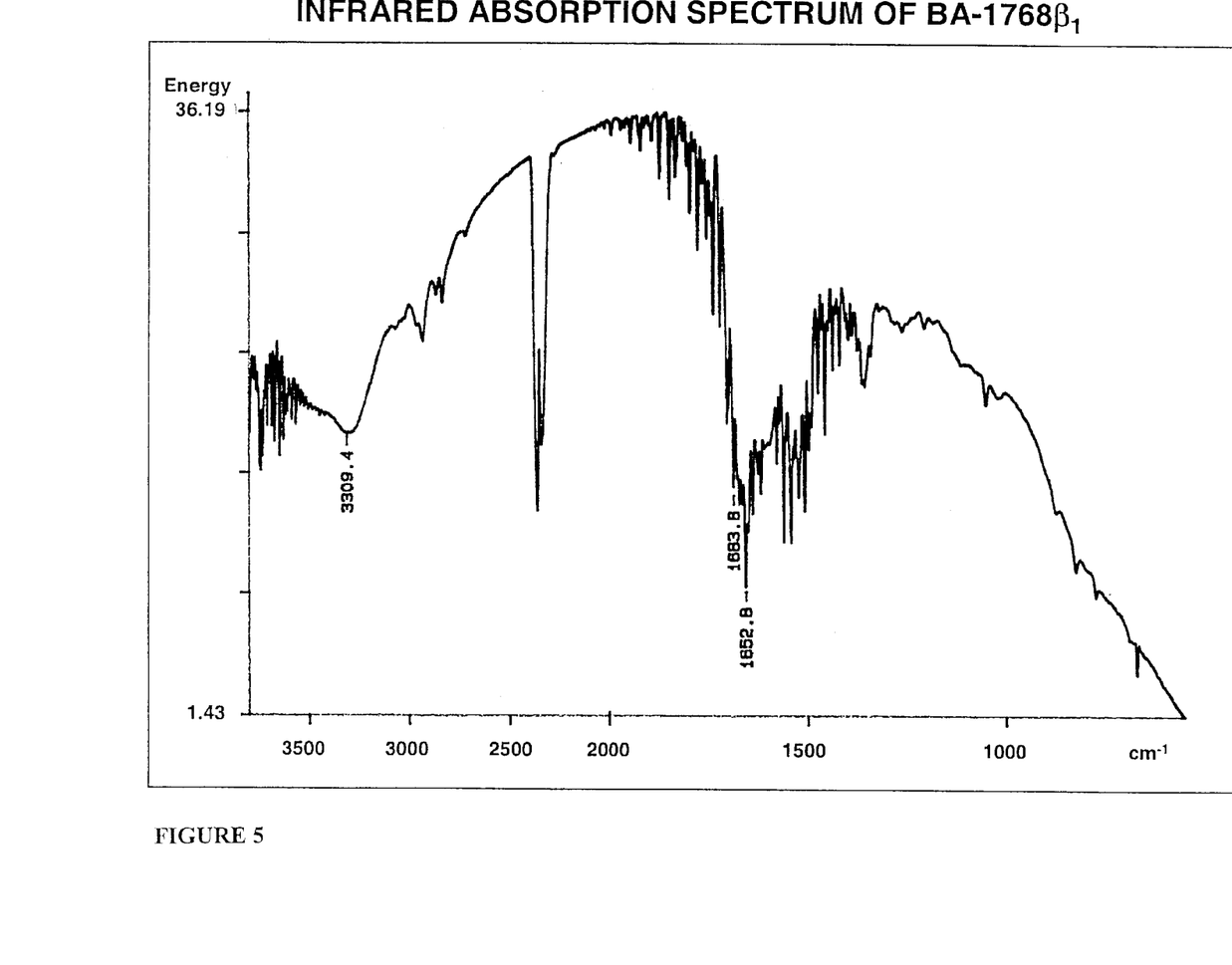
FIG. 5 is the infrared absorption spectrum of MF-BA-1768$\beta_1$ (KBr pellet).
Figure 6:
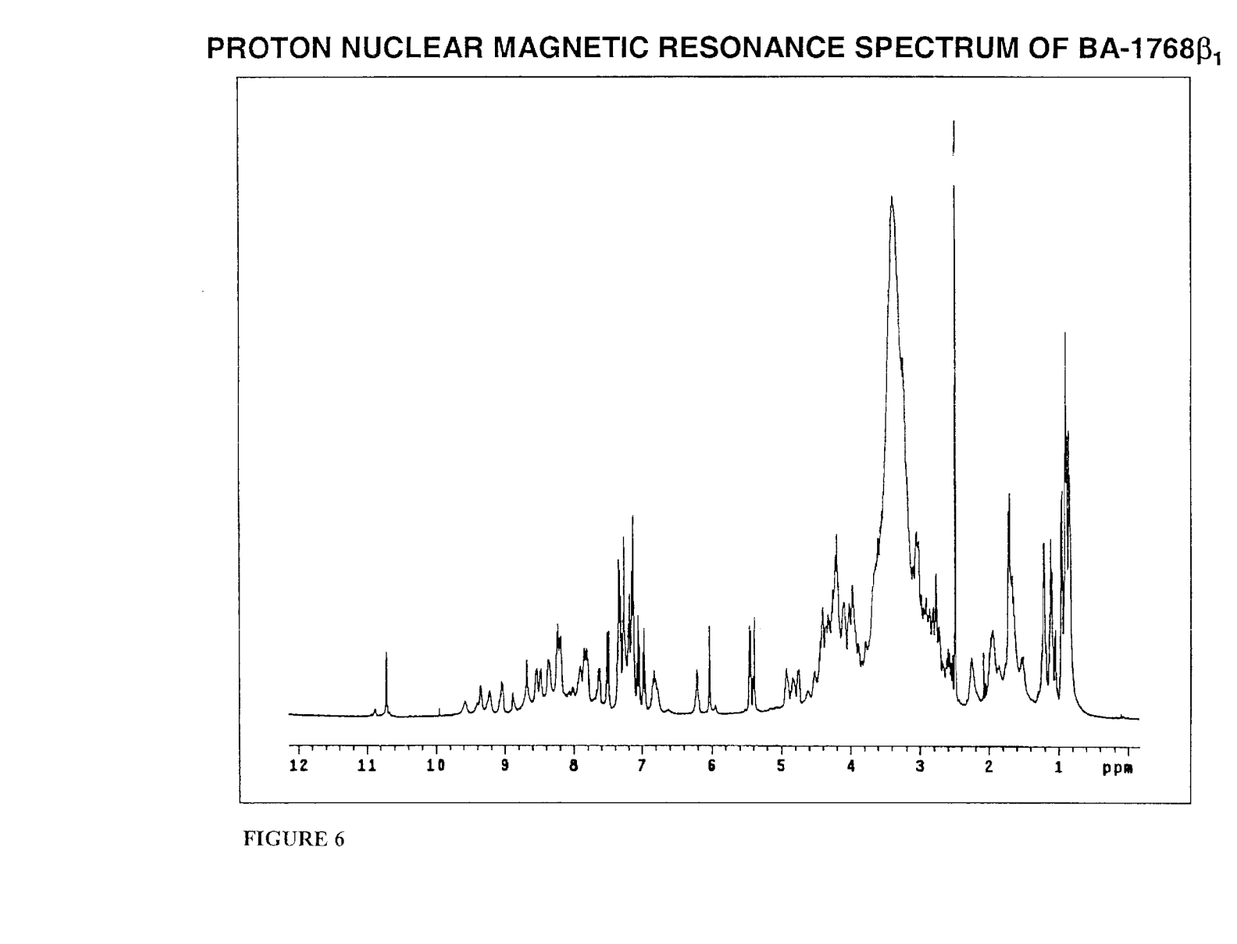
FIG. 6 is the proton magnetic resonance spectrum of MF-BA-1768$\beta_1$ (400 MHz, d$_6$-DMSO, 55° C.).
Figure 7:
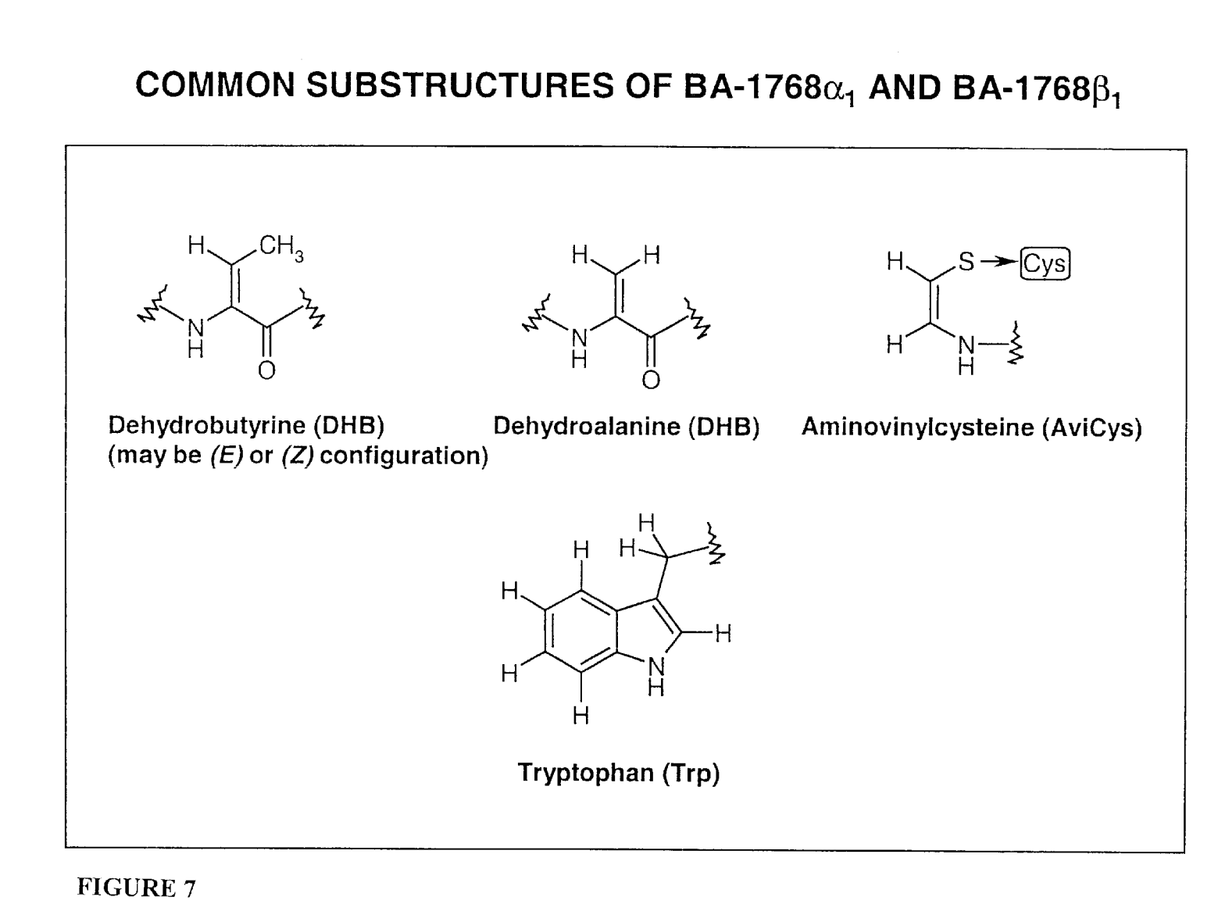
FIG. 7 shows the common substructures of MF-BA-1768$\alpha_1$ and MF-BA-1768$\beta_1$.

Based on the physicochemical characteristics and the spectral evidence in FIGS. 1 through 6, MF-BA-1768α$_1$ and MF-BA-1768β$_1$ are believed to contain the structural features shown in FIG. 7.

General Fermentation Conditions

Cultivation of MF-BA-1768 may be carried out in a wide variety of liquid culture media. In general, media which are useful for the production of compounds MF-BA-1768α$_1$ and MF-BA-1768β$_1$ contain assimilable sources of carbon, such as starch, sugar, molasses, glycerol, etc., assimilable sources of nitrogen such as protein, protein hydrolysate, polypeptides, amino acids, corn steep liquor, etc., and inorganic anions and cations, such as potassium, sodium, ammonium, calcium, sulfate, carbonate, phosphate, chloride, etc. Trace elements such as boron, molybdenum, copper, etc. are supplied as impurities of other constituents of the media. Aeration in fermenters and in flasks is supplied by forcing sterile air through, or onto the surface of, agitated fermentation media. Flask agitation is provided by reciprocal shaking on a mechanical platform. Fermenter agitation is accomplished using a mechanical impeller. An anti-foaming agent such as silicone may be added as needed.

Fermentation is monitored daily for the production of the MF-BA-1768 compounds by LC-MS and the products are harvested when the expected titer is reached.

General Procedure for the Isolation of MF-BA1768$\alpha_1$ and MF-BA1768$\beta_1$ The initial isolation of the BA-1768 compounds was guided by an agar plate assay using a sensitive strain of *Staphylococcus aureus*, MSSA 8325-4. Overnight cultures of MSSA 8325-4 in Mueller-Hinton broth (MHB) were diluted 1:100 (v/v) with fresh MHB and poured onto an agar plate prepared using tryptic soy agar (TSA). After excess inoculum was discarded and plate dried, wells, into which samples of column fractions would be placed, were bored. Assay plates were incubated at 35° C. overnight and column fractions containing zones of inhibition were pooled.

The MF-BA-1768 compounds are present in the fermentation liquor as well as being associated with the cell mass. The compound associated with the cell mass can be recovered by extraction with an organic solvent such as acetone or methanol or mixtures of organic solvent and water such as aqueous acetone. The MF-BA-1768 compounds can be recovered from aqueous solutions by selective adsorption on a polymeric resin such as Diaion® HP-20 (Mitsubishi Chemical Industries Ltd.) and can be desorbed from the resin using an organic solvent or a mixture of organic solvent and water such as, again, aqueous acetone. Separation and purification of the MF-BA-1768 compounds can be accomplished by chromatography on silica based reverse phase chromatographic media such as C-18 or C-8 bonded silica, polymeric reverse phase media such as Amberchrom® (TosoHaas), size exclusion resins such as Sephadex® G-25 (Amersham Pharmacia Biotech), and polyamide resins.

Physico-chemical Properties of MF-BA-1768 Compounds

MF-BA-1768$\alpha_1$

1. Molecular weight: 2214.880, calculated monoisotopic mass from [M+2H]$^{2+}$ at m/z 1108.449, determined by high resolution ESI-FTMS using reference compound peptide mellitin (3$^+$ charge);
2. Ultraviolet absorption spectrum: $\lambda_1$ 223 nm ($\epsilon$=73600, log $\epsilon$=4.87), $\lambda_2$ 270 nm ($\epsilon$=17700, log $\epsilon$=4.25), determined in 35% acetonitrile/0.05% formic acid in water, pH 2.83 (FIG. 1);
3. Infrared absorption spectrum (KBr disc): 3309, 1669 (br) cm$^{-1}$ (FIG. 2);
4. Proton magnetic resonance spectrum: 400 MHz, d$_6$-DMSO, 55° C.; referenced to CD$_3$SOCD$_2$H quintet at 2.50 ppm (FIG. 3);
5. Carbon-13 nuclear magnetic resonance signals were obtained for some carbons based on one-bond $^1$H—$^{13}$C correlation data from HMQC (heteronuclear multiple quantum coherence) experiments. Chemical shifts (in ppm, referenced to CD$_3$SOCD$_2$H heptet at 39.5 ppm, 55° C.), multiplicity (as the number of attached protons), chemical shifts of attached protons, and the COSY correlation of the attach protons of select carbons are tabulated below:

| *Residue | 13C (ppm, multiplicity) | 1H (ppm) | COSY (ppm) |
| --- | --- | --- | --- |
| #Trp | 120.8 (CH) | 7.05 | 7.34 |
| Trp | 126.0 (CH) | 7.19 | 10.89 |
| #Trp | 120.8 (CH) | 7.05 | 7.54 |
| Trp | 117.2 (CH) | 7.54 | 7.05 |
| Trp | 112.8 (CH) | 7.34 | 7.05 |
| Trp | N—H | 10.89 | 7.19 |
| DHB | 126.3 (CH) | 6.21 | 1.72 |
| DHB | 13.0 (CH3) | 1.72 | 6.21 |
| DHA | 103.7 (CH2) | 5.98 | |
| | | 5.40 | |
| AviCys | 130.2 (CH) | 6.83 | 8.38, 5.46 |
| AviCys | 102.5 (CH) | 5.46 | 6.83 |
| AviCys | N—H | 8.38 | 6.83 |

*Trp = tryptophan; DHB = dehydrobutyrine; DHA = dehydroalanine; AviCys = aminovinyl cysteine.
Signals overlapped MF-BA-1768$\beta_1$ 1. Molecular weight: 2180.805, calculated monoisotopic mass from [M+2H]$^{2+}$ at m/z 1091.410, determined by high resolution ESI-FTMS using reference compound peptide mellitin (3$^+$ charge);
2. Ultraviolet spectrum: $\lambda_1$ 221 nm ($\epsilon$=105300, log $\epsilon$=5.02), $\epsilon_2$ 270 nm ($\epsilon$=19300, log $\epsilon$=4.28), determined in 35% acetonitrile/0.05% formic acid in water. (FIG. 4);
3. Infrared absorption spectrum (KBr disc): 3309,1669 cm$^{-1}$ (FIG. 5);
4. Proton magnetic resonance spectrum: 400 MHz, d6-dmso, 55° C.; referenced to CD$_3$SOCD$_2$H quintet at 2.50 ppm (FIG. 6);
5. Carbon-13 nuclear magnetic resonance signals were obtained for some carbons based on one-bond $^1$H—$^{13}$C correlation data from HMQC (heteronuclear multiple quantum coherence) experiments. Chemical shifts (in ppm, referenced to CD$_3$SOCD$_2$H heptet at 39.5 ppm, 55° C.), multiplicity (as the number of attached protons), chemical shifts of attached protons, and the COSY correlation of the attach protons of select carbons are tabulated below:

| *Residue | 13C (ppm, multiplicity) | 1H (ppm) | COSY (ppm) |
| --- | --- | --- | --- |
| Trp | 120.9 (CH) | 7.06 | 7.32 |
| Trp | 128.0 (CH) | 7.12 | 10.71 |
| Trp | 118.2 (CH) | 6.97 | 7.51 |
| Trp | 117.8 (CH) | 7.51 | 6.97 |
| Trp | 111.2 (CH) | 7.32 | 7.06 |
| Trp | N—H | 10.71 | 7.12 |
| DHB | 125.7 (CH) | 6.21 | 1.70 |
| DHB | 12.6 (CH3) | 1.70 | 6.21 |
| DHA | 103.0 (CH2) | 6.04 | |
| | | 5.39 | |
| AviCys | 130.1 (CH) | 6.83 | 8.35, 5.45 |
| AviCys | 102.1 (CH) | 5.45 | 6.83 |
| AviCys | N—H | 8.35 | 6.83 |

*Trp = tryptophan; DHB = dehydrobutyrine; DHA = dehydroalanine; AviCys = aminovinyl cysteine.

Common sub-structures as determined from the C-13 signals and the correlated proton signals in the two tables above are shown in FIG. 7. Based on these substructures and the molecular weight range of 2,100–2,500 Dalton, MF-BA-1768$\alpha_1$ and MF-BA-1768$\beta_1$ are presently thought to be members of the lantibiotic class of antibiotics (Annu. Rev. Microbiol. 1998, 52:41–79).

Biological Activity of MF-BA-1768 Compounds

The antibacterial activity of MF-BA-1768$\alpha_1$ and MF-BA-1768$\beta_1$ were determined against a spectrum of bacterial strains using a broth microdilution assay performed as recommended by the NCCLS (NCCLS Document M7-A4, Vol 17 No.2). With the exception of Streptococci spp. and *H. influenzae*, the assay was performed in Cation Adjusted Mueller-Hinton Broth (CAMHB). For the Streptococci spp., CAMHB+2–5% Laked Horse Blood (REMEL) was used. For *H. influenzae*, Haemophilus Test Medium (REMEL) containing 2% Fildes Enrichment was used. The final bacterial inoculum was 5×10$^5$ CFU/ml in a final assay volume of 100 $\mu$l. Microtiter plates containing the test samples and the respective bacterial inoculum were incubated for 24 hours at 35° C. with the exception of *E. coli* plates, which were incubated for 20 hours at 35° C. Upon completion of incubation, the plates were read using a microtiter plate reader (Molecular Devices) at 650 nm as well as by visual observation using a microtiter plate reading mirror. The minimal inhibitory concentration (MIC) is defined as the lowest concentration of compound at which the visible growth of the organism is completely inhibited. The results are summarized below.

| Antibacterial spectrum of MF-BA-1768 compounds | | | |
|---|---|---|---|
| | | MIC (mcg/ml) | |
| Test Organism | Organism Characteristic | MF-BA-1768$\alpha_1$ | MF-BA-1768$\beta_1$ |
| *Staphylococcus aureus* MSSA 8325-4 | Wild type | 2 | 2 |
| *Staphylococcus aureus* MSSA 8325-4 (serum) | Wild type | 16 | 4 |
| *Staphylococcus aureus* MSSA Smith | Wild type | 2 | 2 |
| *Staphylococcus aureus* MRSA 01A1095 | Clinical isolate | 2 | 0.5 |
| *Staphylococcus epidermidis* MRSE 5 | Clinical isolate/ Erythromycin$^R$ | 8 | 16 |
| *Staphylococcus haemolyticus* UA281 (BM4624) | Clinical isolate | 32 | 32 |
| *Enterococcus faecalis* VanA (efs 097) | Vancomycin$^R$ | 16 | 32 |
| *Enterococcus faecalis* VanB (efs 010) | Vancomycin$^R$ | 8 | 32 |
| *Enterococcus faecium* Van$^R$ (efm 129) | Clinical isolate | 16 | 64 |
| *Enterococcus faecium* A491 | Clinical isolate/ Ampicillin$^R$ | 16 | 32 |
| *Streptococcus pneumoniae* 02J1095 | Clinical isolate | </=0.25 | </=0.25 |
| *Streptococcus pneumoniae* 670 | Clinical isolate | </=0.25 | </=0.25 |
| *Streptococcus pyogenes* ATCC12384 | Wild type | </=0.25 | </=0.25 |
| *Haemophilus influenzae* 54A1100 | Clinical isolate | 8 | 16 |
| *Haemophilus influenzae* E-170 | PBP alteration/ Ampicillin$^R$ | 64 | 64 |
| *Escherichia coli* imp4213 | Hyper-susceptible | 1 | 0.5 |
| *Escherichia coli* 51A1056 | Clinical isolate | >128 | >128 |

The antibacterial activity of MF-BA-1768$\beta_1$ was further evaluated side-by-side with 9 reference antibiotics against a collection of genotypically well-characterized isolates of *Staphylococcus aureus*. These included 64 MRSA (methicillin resistance *Staphylococcus aureus*) strains and 19 MSSA (methicillin sensitive *Staphylococcus aureus*) strains representing 57 staphylococcal protein A genotypes and 22 coagulase A genotypes. The most common protein A genotypes found in the USA were represented by more than one isolate. The results obtained are shown in the following table as MIC$_{50}$ (concentration at which visible growth of 50% of a group of strains are completely inhibited) and MIC$_{90}$ (concentration at which visible growth of 90% of a group of strains are completely inhibited).

| | MRSA (64 strains) | | MSSA (19 strains) | |
|---|---|---|---|---|
| Test Compound | MIC$_{50}$ (mcg/ml) | MIC$_{90}$ (mcg/ml) | MIC$_{50}$ (mcg/ml) | MIC$_{90}$ (mcg/ml) |
| MF-BA-1768$\beta_1$ | 2 | 4 | 1 | 2 |
| Vancomycin | 0.5 | 1 | 0.5 | 1 |
| Ofloxacin | 0.5 | 32 | 0.5 | 32 |
| Rifampicin | <=0.0625 | >32 | <=0.0625 | <=0.0625 |
| Gentamicin | 1 | >32 | 0.5 | 32 |
| Tetracycline | 0.25 | >32 | 0.25 | 32 |
| Oxacillin | 128 | 512 | <=1 | 64 |
| Imipenem | 8 | 128 | <=0.5 | 4 |
| Cefotaxime | 512 | >512 | 2 | 256 |
| Nafcillin | 64 | 256 | <=1 | 16 |

EXAMPLES

Example 1

Preparation of MF-BA-1768 Culture Master Stock

A small amount of culture MF-BA-1768 was plated on 100×15 mm Petri dish containing a sterilized plating medium having the following composition.

| Plating Medium | |
|---|---|
| Agar | 20.9 grams/liter |
| Malt extract | 10.0 grams/liter |
| Yeast extract | 4.0 grams/liter |
| Glucose | 4.0 grams/liter |
| L-arginine | 0.3 grams/liter |

After incubation at 28° C. for 12 to 15 days, the mixture of spores and mycelia on the plate were harvested with a 15% sterile solution of glycerol. The suspension was partitioned into 1 ml vials and stored at minus 80° C.

Example 2

Preparation of Inoculum for the Production of MF-BA-1768 Compounds

The medium used for the inoculum, consisting of the following ingredients, was sterilized at 121° C. for 20 minutes.

| Inoculum (Seed) Medium | |
|---|---|
| Glucose | 10.0 grams/liter |
| Soluble starch | 20.0 grams/liter |
| NZ Amine, type A | 10.0 grams/liter |
| Beef extract | 10.0 grams/liter |

-continued

| Inoculum (Seed) Medium | |
| --- | --- |
| Peptone | 10.0 grams/liter |
| Yeast extract | 10.0 grams/liter |
| Calcium carbonate | 3.0 grams/liter |
| Prepared with deionized water | |
| Adjusted to pH 7.0 prior to addition of calcium carbonate | |

S1 inoculum: A suspension of spores and mycelia of MF-BA-1768 was prepared in sterile 10% glycerol solution from a plate freshly prepared as described in Example 1. A 2-ml portion of the suspension was inoculated into 50-ml of the seed medium in a 250-ml Erlenmeyer flask. The inoculated flask was incubated for 45–48 hours at 28° C., 85% relative humidity, on a reciprocating shaker (2-inch throw, 220 revolutions per minute (rpm)) to give the S1 inoculum.

S2 inoculum:. A 33-ml portion of the S1 inoculum was inoculated into 150-ml of the seed medium in a 500-ml Erlenmeyer flask. The inoculated flask was incubated for 22–24 hours at 28° C., 85% relative humidity on a reciprocating shaker (2-inch throw, 160 rpm) to give the S2 inoculum.

Example 3

Production of the MF-BA-1768 Compounds in 250-ml Flasks

The following fermentation medium used to obtain the MF-BA-1768 compounds. After preparation, it was sterilized at 121° C. for 20 minutes.

| Production Medium | |
| --- | --- |
| Fructose | 40.0 grams/liter |
| Soybean hydrolyzate | 20.0 grams/liter |
| Yeast extract | 10.0 grams/liter |
| Calcium carbonate | 3.0 grams/liter |
| Prepared with deionized water | |
| Adjusted to pH 7.0 prior to addition of calcium carbonate | |

Three Erlenmeyer flasks containing 45 ml of the production medium were each inoculated with 2 ml of the S1 inoculum prepared as described in Example 2. Fermentation was conducted by incubating the inoculated flasks at 28° C. and 85% relative humidity on a reciprocating shaker (2-inch throw, 220 rpm). Fermentation was terminated after 4, 7, and 11 days of incubation.

Example 4

Production of the MF-BA-1768 Compounds in 2.8-L Fernbach Flasks

Five 2.8-L Fernbach flasks containing 500 ml of sterilized production medium prepared as described in Example 3 were each inoculated with 20 ml of the S1 inoculum prepared as described in Example 2. Fermentation was conducted by incubating the inoculated flasks at 28° C. and 85% relative humidity on a reciprocating shaker (2-inch throw, 160 rpm). The fermentation was terminated after 10–12 days and the contents of the flasks were combined and centrifuged. The MF-BA-1768 compounds were present in the supernatant and in the cell pellet. The mycelia of the 2.5 liters of harvested whole mash was collected by centrifugation, extracted with 1.0 liter of acetone-water (9:1) and centrifuged to remove cell debris. The extract was concentrated in vacuo to give an aqueous suspension that was combined with the 2 liters of the fermentation supernatant for further processing as described in Example 7.

Example 5

Production of the MF-BA-1768 Compounds in 20-L Fermenter

Six 500-ml Erlenmeyer flasks, each containing 180 ml of the S2 inoculum prepared as described in Example 2, were inoculated into 12-liters of production medium prepared as described in Example 3 in a 20-L fermenter. The mixture was incubated at 28° C. with 5 liters per minute (Ipm) aeration and dissolved oxygen was maintained at 40% saturation by adjusting the impeller agitation rate. The production of MF-BA-1768 compounds was monitored by LC-MS and the fermentation was harvested when the desired titer was reached, between 8 and 15 days. The mycelia of the 12 liters of harvested whole mash were collected by centrifugation and extracted with 4.0 liters of acetone-water (9:1). After removal of the cell debris by centrifugation, the extract was evaporated in vacuo to give 800 ml of an aqueous suspension, which was combined with the 11 liters of fermentation supernatant and further processed as described in Example 8.

Example 6

Preliminary Identification of the Antibiotic Activity Produced by MF-BA-1768 Compounds A small portion of the MF-BA-1768 complex prepared as described in Example 7 was fractionated using the following chromatographic conditions:

| Time | Solvent mixture A/B |
| --- | --- |
| 0 min | 20/80 |
| 1 min | 20/80 |
| 20 min | 100/0 |
| 24min | 100/0 |

Column: C18 100 10sp, 10 × 0.46 cm (10 µm spherical particle, 100 angstrom pore, Amicon, Inc.)
Solvent: A = methanol; B = 20 mM ammonium acetate (pH 5.0)
Flow rate: 1 ml/min
Detection: 254 nm
Retention: Multiple components, range 15 to 18 min.

Fractions were collected every 0.5 minute and 20 µl of each was assayed against S. aureus MSSA 8325-4 as described above. The assay showed multiple active components in the 15–18 minute fractions. The molecular weights of these compounds, initially determined by positive ion electrospray ionization mass spectrometry (ESI-MS), were in the 1000–1200 Da range, or some multiple of these values due to the possibility of multiple charges when using ESI-MS. These components were deemed to be related because of their virtually identical UV spectra.

Example 7

Purification of MF-BA-1768$\alpha_1$ from Original 2.5 L Fermentation

The MF-BA-1768 compounds contained in the mixture of mycelial extract and fermentation supernatant prepared in Example 4 were adsorbed onto a 22×2.5 cm HP-20 column by passing the mixture through the column at 6 ml/min. The column was then washed with 3 bed volumes of deionized water and eluted with the following water/acetone gradient:

| Time | Solvent mixture A/B, v/v |
|---|---|
| 0 min | 0/100 |
| 20 min | 0/100 |
| 40 min | 20/80 |
| 110 min | 20/80 |
| 220 min | 100/0 |
| 330 min | 100/0 |

Solvent A = Acetone, Solvent B = Water
Flow rate: 5 ml/min

Fractions were collected every 4 minutes and assayed using *S. aureus* MSSA 8325-4. Fractions 36–54 were combined and concentrated to give 347 mg of crude MF-BA-1768 complex. This sample was re-suspended in 5 ml 50% methanol-water, and chromatographed on a 21×1.8 cm C18 column (Amicon, 40 μm particle size) using the following gradient:

| Time | Solvent mixture A/B, v/v |
|---|---|
| 0 min | 40/60 |
| 10 min | 40/60 |
| 50 min | 100/0 |
| 70 min | 100/0 |

C18 column; Solvent A = Methanol, Solvent B = Water;
Flow rate: 8 ml/min;
Detection: 254 nm Fractions of 16 ml were collected, and the active fractions (16 to 35) were combined to yield 147 mg of enriched MF-BA-1768 complex. This material was further purified by re-suspension in 3 ml 33% acetonitrile/water and chromatography on a 24×1.8 cm C18 column (Amicon, 40 μm) using acetonitrile/water/TFA (pH 3.2):

| Time | Solvent mixture A/B, v/v |
|---|---|
| 0 min | 20/80 |
| 8 min | 20/80 |
| 15 min | 30/70 |
| 30 min | 30/70 |
| 160 min | 60/40 |

Solvent A = Acetonitrile; Solvent B = Water + trifluoroacetic acid, pH 3.2
Flow rate: 8 ml/min
Detection: 254 nm Twenty milliliter fractions were collected and assayed against *S. aureus* MSSA 8325-4. Based on the assay, the fractions were combined into three pools containing different ratios of the MF-BA-1768 components: fractions 8–13 (60 mg), fractions 14–19 (34 mg), and fractions 20–26 (30 mg). Material from fractions 14–19 and fractions 20–26 were separately chromatographed using a C18 semi-preparative column (Amicon, 25 cm×1 cm, 10 μm particle size), each employing 6 injections of 100 μl (in 1:1 acetonitrile-water) and collecting 0.5 min fractions. The chromatography conditions were:

| Time | Solvent mixture A/B, v/v |
|---|---|
| 0 min | 30/70 |
| 3 min | 30/70 |
| 30 min | 60/40 |
| 32 min | 100/0 |
| 40 min | 100/0 |

Solvent A = Acetonitrile; Solvent B = Water + trifluoroacetic acid, pH 3.2
Flow rate: 4.7 ml/min
Detection: 254 nm To obtain the best yield of a single component, fractions containing ESI-MS peak m/z 1109 Da were combined (fractions 36–40). Total yield from these fractions was 6 mg of analytically pure MF-BA-1768$\beta_1$. With this sample, a higher resolution scan at m/z 1109 Da was obtained on a Finnigan LCQ Deca ESI mass spectrometer, which showed that the ion is a double charged species. Thus, the true molecular weight of this compound is 2214.8 Da (monoisotopic mass).

Example 8

Purification of MF-BA-1768$\beta_1$ from Follow-up 12.0 L Fermentation

The MF-BA-1768 compounds contained in the 12 liters of combined mycelial extract and fermentation supernatant prepared as described in Example 5 were adsorbed onto a 25×4.5 cm HP-20 column by passing the mixture through the column at 8 ml/min. The charged column was washed with 2000 ml deionized water and then eluted using the following water/acetone gradient.

| Time | Solvent mixture A/B, v/v |
|---|---|
| 0 min | 0/100 |
| 20 min | 20/80 |
| 220 min | 20/80 |
| 420 min | 100/0 |
| 550 min | 100/0 |

Solvent A = Acetone, Solvent B = Water; Flow rate: 10 ml/min

The 25-ml fractions collected during the elution were assayed against *S. aureus* SAM 23 and fractions 119–163 were combined to yield 2.0 grams of crude MF-BA-1768 complex. From this sample, a modified analytical HPLC method was developed that was used for all subsequent analyses. This presently preferred separation protocol uses a PLRPs column and acetonitrile (Solvent A) and 0.05% Formic Acid in Water (pH 2.83) (solvent B) as eluent under the following gradient scheme:

| Time | Solvent mixture A/B, v/v |
|---|---|
| 0 min | 25/75 |
| 2 min | 25/75 |
| 10 min | 38/62 |
| 20 min | 38/62 |

Column: 15.0 × 0.46 cm PLRPs (Polymer Labs, 5 um)
Flow rate: 1 ml/min
Detection: 254 nm
Retention times: various MF-BA-1768 components, 8–13 min
BA-1768$\alpha_1$ 9.1 min
BA-1768$\beta_1$ 10.6 min Under the above conditions, the crude MF-BA-1768 complex showed one major component (m/z 1092 Da in LC-MS) that could be separated from the other component due to its greater polarity. The 2.0 g sample of MF-BA-1768 complex was re-suspended in 500 ml 15% acetonitrile/ 0.05% formic acid in water (pH 2.83) and loaded onto a 26×2.5 cm Amberchrom CG-161md column (TosoHaas, 50–100 μm) pre-equilibrated in 15:85, acetonitrile-0.05% formic acid. The loaded column was eluted using the following gradient:

| Time | Solvent mixture A/B, v/v |
|---|---|
| 0 min | 15/85 |
| 30 min | 15/85 |
| 160 min | 45/55 |
| 210 min | 45/55 |

Amberchrom column; Solvent A = Acetonitrile; Solvent B = 0.05% Formic Acid in Water (pH 2.83)
Flow rate: 8 ml/min
Detection: 254 nm Fractions (24 ml each) collected during the elution were assayed against *S. aureus* MSSA 8325-4 as well as being analyzed by HPLC. The fractions (35–38) enriched in the m/z 1092 Da component (as shown by HPLC, $R_t$=9.1 min, MF-BA-1768$\beta_1$ were combined and worked up to give 179 mg enriched MF-BA-1768$\beta_1$. The less polar MF-BA-1768 components were pooled (fractions 45–54) as MF-BA-1768$\alpha_n$ complex (472 mg), which includes the previously isolated MF-BA-1768$\alpha_1$.

The MF-BA-1768$\alpha_n$ complex was decolorized with polyamide resin (Macherey-Nagel). The 472 mg of material obtained were dissolved in 430 ml 50% acetonitrile/water and vacuum filtered through a 75-ml bed of dry polyamide in a sintered glass funnel. The filtrate was collected as one batch. The column was washed with two 200 ml 50% acetonitrile/water washes and a final 200 ml acetonitrile wash, the washes being kept separate for the initial filtrate and from each other. Each wash was analyzed by HPLC. Based on the HPLC, the initial filtrate and the 50% acetonitrile-water washes were combined, rotary evaporated, and freeze-dried. Final de-colorization was achieved by trituration with 10-ml portions of water. The white precipitate obtained was collected by centrifugation and freeze-dried to yield 282 mg of MF-BA-1768$\alpha_n$.

The 179 mg of enriched MF-BA-1768$\beta_1$ was also de-colorized using polyamide resin as described above. The sample was then dissolved in 100 ml water and vacuum filtered through a 75 ml dry bed of polyamide. The polyamide bed was washed with 500 ml water followed by three more 100 ml water portions and finally 300 ml of 50% acetonitrile/water. HPLC showed that the initial filtrate and the 500-ml water wash were highly enriched in MF-BA-1768$\beta_1$ and yielded 139 mg of partially purified product upon work-up. Analysis using a light scattering detector showed that the sample contains a non-UV active impurity. LC-MS showed that the impurity to be a low molecular weight component (446 Da). The partially purified MF-BA-1768$\beta_1$ was dissolved in 8 ml 10% methanol/water and loaded on a 45×2.5 cm Sephadex G-25 column (10% methanol/water at 1.5 ml/min). The fractions (8 min each) collected were analyzed by HPLC. Based on the HPLC, fractions 16–26 were combined and worked up to give 28 mg of analytically pure MF-BA-1768$\beta_1$.

CONCLUSION

Thus, the present invention, as described above, provides a novel strain of *Microbispora corallina*, means for identifying it, methods for culturing it at several different levels, two new antibiotics derived from the cultures and the physico-chemical characteristics and biological activity of those compounds against a variety of microorganisms.

SEQUENCE LISTING

<160> NUMBER OF SEQ ID NOS: 1

<210> SEQ ID NO 1
<211> LENGTH: 1584
<212> TYPE: DNA
<213> ORGANISM: Microbispora corallina
<220> FEATURE:
<221> NAME/KEY: n
<222> LOCATION: (1350)..(1584)
<223> OTHER INFORMATION: Unsure
<221> NAME/KEY: misc_feature
<222> LOCATION: (1350)..(1584)
<223> OTHER INFORMATION: Unsure

<400> SEQUENCE: 1

```
aggctggatc acctcctttc tagctggatg agtttgatcc tggctcaggc tggatcacct      60
cctttctagc tggatgagtt tgatcctggc tcaggacgaa cgctggcggc gtgcttaaca     120
catgcaagtc gagcggaaag gcccttcggg gtactcgagc ggcgaacggg gagtaacacg     180
tgagtaacct gcccctgact ctgggataag cctgggaaac cgggtctaat accggatatg     240
acacatggtc gcatgagcgg tgtgtggaaa gttttttcgg ttggggatgg gctcgcggcc     300
tatcagcttg ttggtggggt gatggcctac caaggcgacg acgggtagcc ggcctgagag     360
ggcgaccggc cacactggga ctgagacacg gcccagactc ctacgggagc agcagtgggg     420
```

-continued

```
aatattgcgc aatgggcgga agcctgacgc agcgacgccg cgtgggggtg acggccttcg    480
ggttgtaaac ctctttcagc agggacgaag ttgacgtgta cctgtagaag aagcgccggc    540
taactacggt gccagcagcc gcggtaatac gtagggcgca agcgttgtcc ggaattattg    600
ggcgtaaaga gctcgtaggt ggcttgttgc gtctgccgtg aaagcccgtg gcttaactac    660
gggtctgcgg gtgaatacgg gcaggctaga ggctggtagg gcaagcgaat tcctggtgta    720
gcggttaaat gcgcagatat caggaggaac accggtgcga aggcggcttg ctggccagtt    780
ctgacgctga ggagcgaaag cgtggggagc gaacaggatt agatacctg gtagtccacg     840 ctgtaaacgt tgggcgctag gtgtgggggt cttccacgat tcctgtgccg tagctaacgc    900
attaagcgcc ccgcctgggg agtacggccg caaggctaaa actcaaagga attgacgggg    960
gcccgcacaa gcggcggagc atgttgctta attcgacgca acgcgaagaa ccttaccaag   1020
gtttgacata caccggaaag ctctggagac agagccctcc tttggactgg tgtacaggtg   1080
gtgcatggct gtcgtcagct cgtgtcgtga gatgttgggt taagtcccgc aacgagcgca   1140 accctgttc catgttgcca gcacgccttc gggtggtggg gactcatggg agactgccgg    1200
ggtcaactcg gaggaaggtg gggatgacgt caagtcatca tgccccttat gtcttgggct   1260
gcaaacatgc tacaatggtc ggtacagagg gttgcgatgc cgtgagtgga gcgaatccyw   1320
aaaagccggt ctcagttcgg attggggtcn tgcaactckr mmmccatgaa agtcggagtc   1380
gcntmgtaat cgcagatcag caacgcttgc ggtgaatacg ttnccgggcc tttgtacaca   1440
ccggcccgtc acgttacgaa aagtcggcaa caccccgaaa gcccgtnggc caaccacttt   1500 tgggggggaac cgtccaaagg tggggcttgg caattgggac naaatcntaa caaggtaacc   1560
ctncccggaa ggtccggttg gntc                                           1584
```

Figure 1:
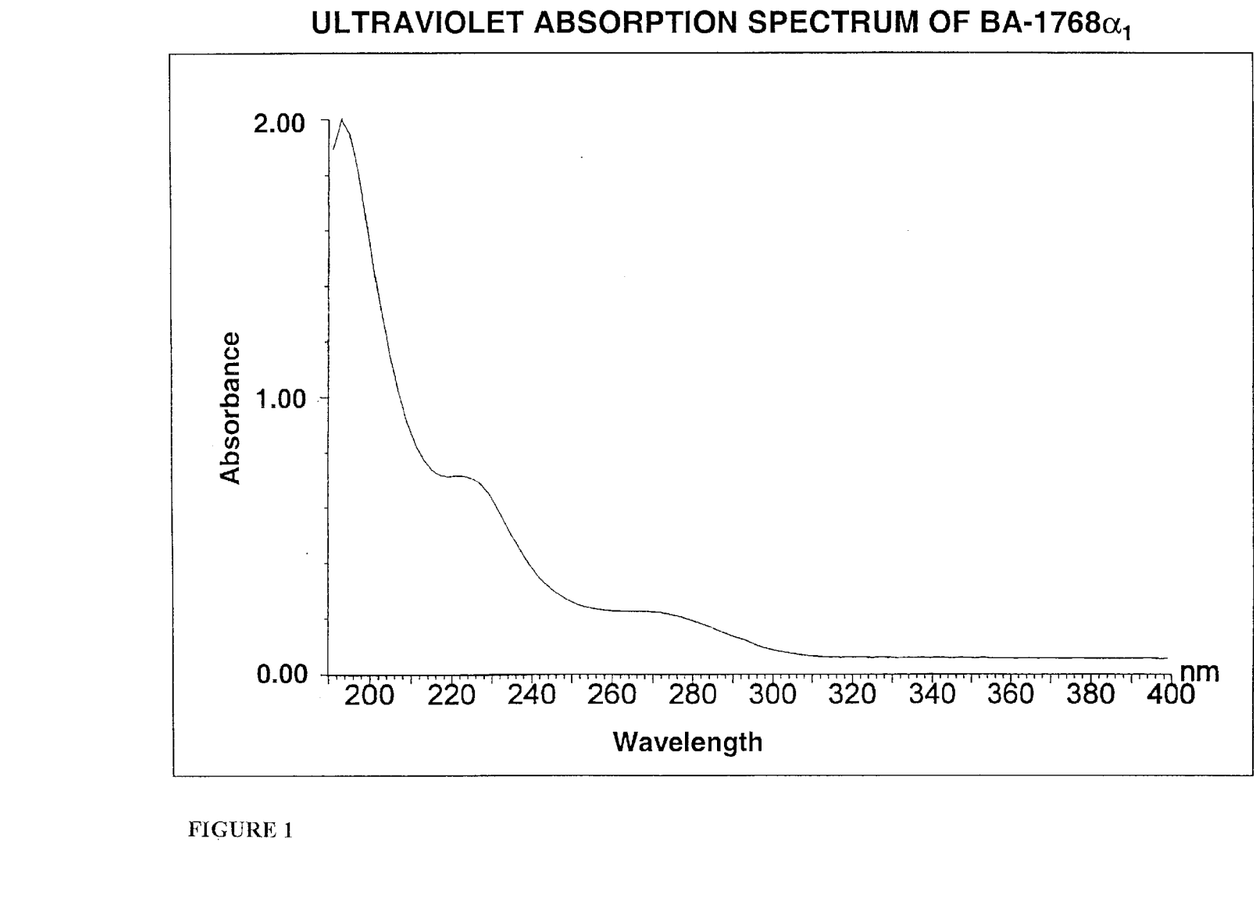
FIG. 1 is the ultraviolet absorption spectrum of MF-BA-1768$\alpha_1$ (0.025 µg/ml solution in 35% acetonitrile-0.05% formic acid in water, pH 2.83).
Figure 2:
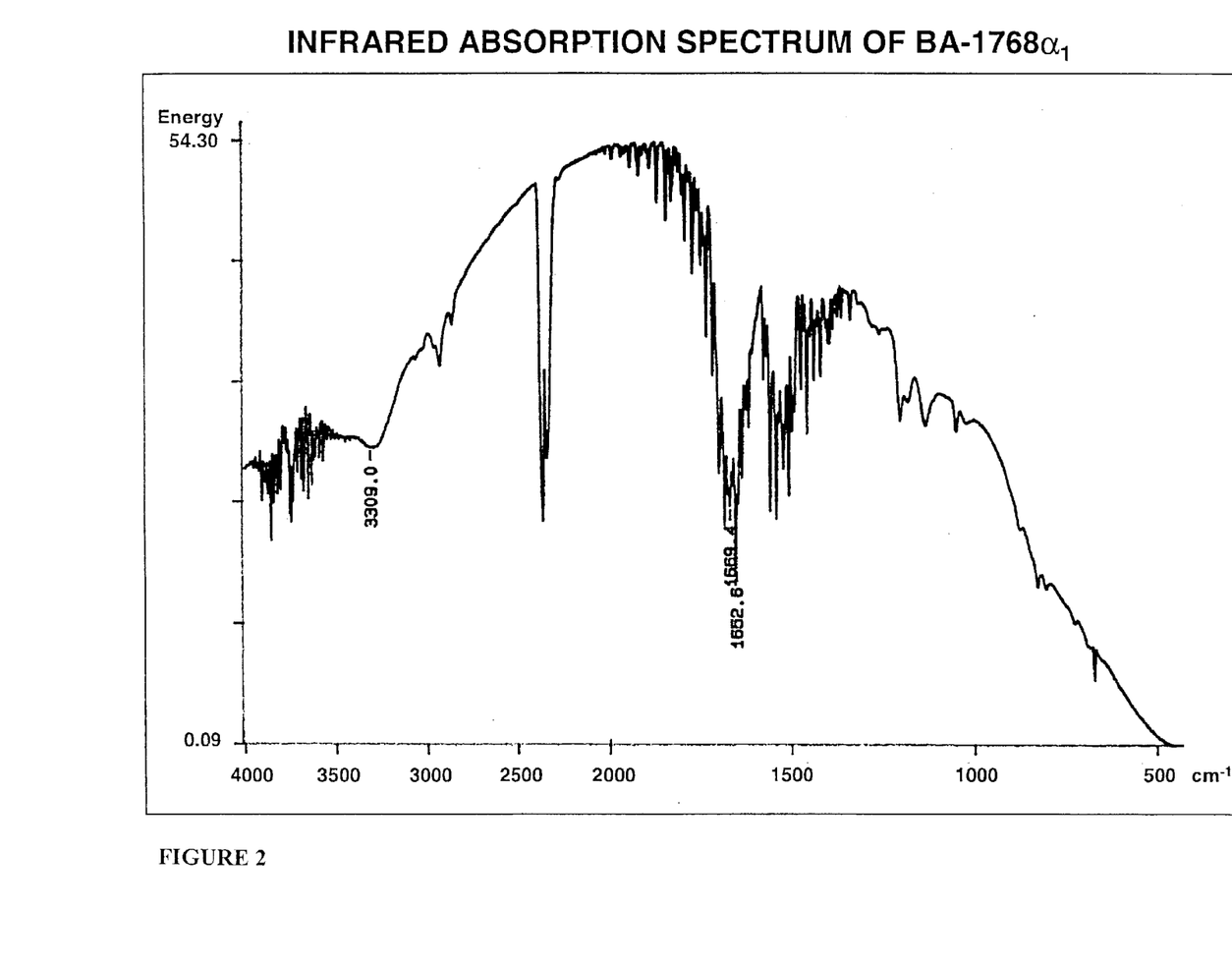
FIG. 2 is the infrared absorption spectrum of MF-BA-1768$\alpha_1$ (KBr pellet).
Figure 3:
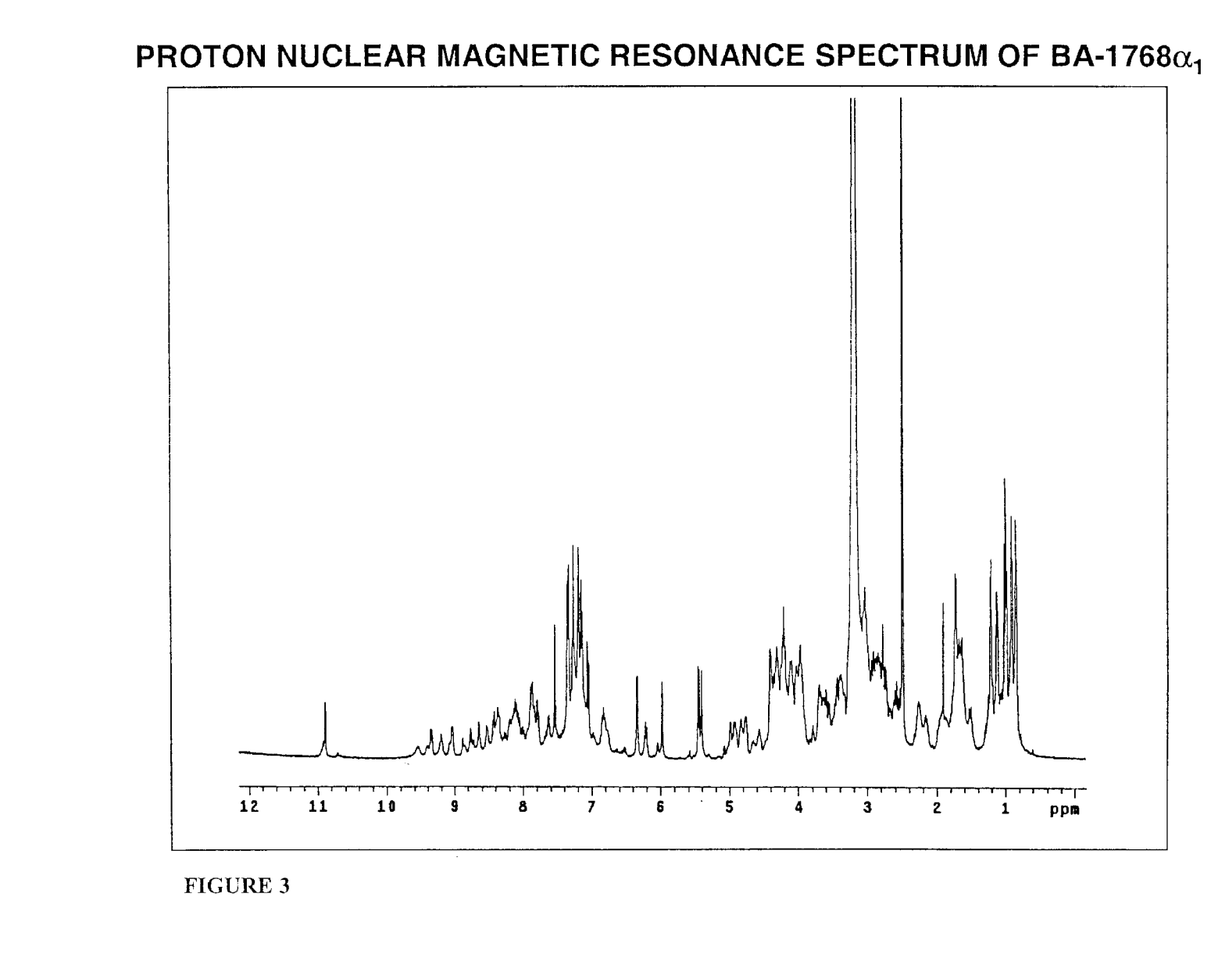
FIG. 3 is the proton magnetic resonance spectrum of MF-BA-1768$\alpha_1$ (400 MHz, d$_6$-DMSO, 55° C.).

What is claimed:

1. Antibiotic MF-BA-1768α₁, or a pharmaceutically acceptable salt thereof, having the following physicochemical characteristics in the non-salt form:

a. molecular weight: 2214.880, calculated monoisotopic mass from $[M+2H]^{2+}$ at m/z 1108.449, determined by high resolution ESI-FTMS using reference compound peptide mellitin ($3^+$ charge);

b. ultraviolet absorption spectrum shown in FIG. 1, comprising absorption maxima at $\lambda_1$=223 nm ($\epsilon$=73600, log $\epsilon$=4.87) and $\lambda_2$=270 nm ($\epsilon$=17700, log $\epsilon$=4.25);

c. infrared absorption spectrum shown in FIG. 2, comprising absorption maxima at 3309 and 1669 (br) cm$^{-1}$ (KBr disc);

d. proton magnetic resonance spectrum shown in FIG. 3 (400 MHz, d₆-DMSO, 55° C.; referenced to CD₃SOCD₂H quintet at 2.50 ppm);

e. carbon-13 nuclear magnetic resonance signals comprising the following chemical shifts (in ppm, referenced to CD₃SOCD₂H heptet at 39.5 ppm, 55° C.), multiplicities (as the number of attached protons), chemical shifts of attached protons, and the COSY correlation of attached protons of select carbons:

| *Residue | ¹³C (ppm, multiplicity) | 1H (ppm) | COSY (ppm) |
|---|---|---|---|
| #Trp | 120.8 (CH) | 7.05 | 7.34 |
| Trp | 126.0 (CH) | 7.19 | 10.89 |
| #Trp | 120.8 (CH) | 7.05 | 7.54 |
| Trp | 117.2 (CH) | 7.54 | 7.05 |
| Trp | 112.8 (CH) | 7.34 | 7.05 |
| Trp | N—H | 10.89 | 7.19 |
| DHB | 126.3 (CH) | 6.21 | 1.72 |
| DHB | 13.0 (CH3) | 1.72 | 6.21 |
| DHA | 103.7 (CH2) | 5.98 | |
| | | 5.40 | |
| AviCys | 130.2 (CH) | 6.83 | 8.38, 5.46 |
| AviCys | 102.5 (CH) | 5.46 | 6.83 |
| AviCys | N—H | 8.38 | 6.83 |

*Trp = tryptophan; DHB = dehydrobutyrine; DHA = dehydroalanine; AviCys = aminovinyl cysteine.
Signals overlapped f. retention time of 9.1 minutes when chromatographed under the following conditions:

Column: 15.0×0.46 cm PLRPs (Polymer Labs, 5 um)

Flow rate: 1 ml/min

Detection: 254 nm

Eluant: acetonitrile (Solvent A) 0.05% Formic Acid in Water (pH 2.83) (solvent B)

Protocol: the following solvent ratios and gradient:

| Time | Solvent mixture A/B, v/v |
| --- | --- |
| 0 min | 25/75 |
| 2 min | 25/75 |
| 10 min | 38/62 |
| 20 min | 38/62. |

2. Antibiotic MF-BA-1768$\beta_1$, or a pharmaceutically acceptable salt thereof, having the following physicochemical characteristics in the non-salt form:
   a. molecular weight: 2180.805, calculated monoisotopic mass from [M+2H]$^{2+}$ at m/z 1091.410, determined by high resolution ESI-FTMS using reference compound peptide mellitin (3$^+$ charge);
   b. ultraviolet spectrum shown in FIG. 4, comprising absorption maxima at $\lambda_1$ 221 nm ($\epsilon$=105300, log $\epsilon$=5.02) and $\lambda_2$ 270 nm ($\epsilon$=19300, log $\epsilon$=4.28);
   c. infrared absorption spectrum shown in FIG. 5, comprising absorption maxima at 3309 and 1669 cm$^{-1}$ (KBr disc);
   d. proton magnetic resonance spectrum shown in FIG. 6 (400 MHz, d$_6$-dmso, 55° C.; referenced to CD$_3$SOCD$_2$H quintet at 2.50 ppm);
   e. carbon-13 nuclear magnetic resonance signals comprising the following chemical shifts (in ppm, referenced to CD$_3$SOCD$_2$H heptet at 39.5 ppm, 55° C.), multiplicities (as the number of attached protons), chemical shifts of attached protons, and COSY correlation of the attached protons of select carbons:

| *Residue | 13C (ppm, multiplicity) | 1H (ppm) | COSY (ppm) |
| --- | --- | --- | --- |
| Trp | 120.9 (CH) | 7.06 | 7.32 |
| Trp | 128.0 (CH) | 7.12 | 10.71 |
| Trp | 118.2 (CH) | 6.97 | 7.51 |
| Trp | 117.8 (CH) | 7.51 | 6.97 |
| Trp | 111.2 (CH) | 7.32 | 7.06 |
| Trp | N—H | 10.71 | 7.12 |
| DHB | 125.7 (CH) | 6.21 | 1.70 |
| DHB | 12.6 (CH3) | 1.70 | 6.21 |
| DHA | 103.0 (CH2) | 6.04 | |
| | | 5.39 | |
| AviCys | 130.1 (CH) | 6.83 | 8.35, 5.45 |
| AviCys | 102.1 (CH) | 5.45 | 6.83 |
| AviCys | N—H | 8.35 | 6.83 |

*Trp = tryptophan; DHB = dehydrobutyrine; DHA = dehydroalanine; AviCys = aminovinyl cysteine.

f. retention time (R$_t$) of 10.6 minutes when chromatographed under the following conditions:
     Column: 15.0×0.46 cm PLRPs (Polymer Labs, 5 um)
     Flow rate: 1 ml/min
     Detection: 254 nm
     Eluant: acetonitrile (Solvent A) 0.05% Formic Acid in Water (pH 2.83) (solvent B)
     Protocol: the following solvent ratios and gradient:

| Time | Solvent mixture A/B, v/v |
| --- | --- |
| 0 min | 25/75 |
| 2 min | 25/75 |
| 10 min | 38/62 |
| 20 min | 38/62. |

3. A process for producing antibiotic MF-BA-1768$\alpha_1$, comprising cultivating a strain of *Microbispora corallina*, NRRL 30420, or an antibiotic MF-BA-1768$\alpha_1$-producing mutant, variant or recombinant form thereof, in a culture medium containing assimilable sources of carbon, nitrogen and inorganic salts under aerobic fermentation conditions until antibiotic MF-BA-1768$\alpha_1$ is produced and then recovering the antibiotic therefrom.

4. A process for producing antibiotic MF-BA-1768$\beta_1$, comprising cultivating a strain of *Microbispora corallina*, NRRL 30420, or an antibiotic MF-BA-1768$\beta_1$-producing mutant, variant or recombinant form thereof, in a culture medium containing assimilable sources of carbon, nitrogen and inorganic salts under aerobic fermentation conditions until antibiotic MF-BA-1768$\beta_1$ is produced and then recovering the antibiotic therefrom.

5. A composition comprising:
   a therapeutically effective amount of compound MF-BA-1768$\alpha_1$ or a pharmaceutically acceptable salt thereof; and,
   a pharmaceutically acceptable carrier,
   wherein compound MF-BA-1768$\alpha_1$ has the following physicochemical characteristics:
     a. molecular weight: 2214.880, calculated monoisotopic mass from [M+2H]$^{2+}$ at m/z 1108.449, determined by high resolution ESI-FTMS using reference compound peptide mellitin (3$^+$ charge);
     b. ultraviolet absorption spectrum shown in FIG. 1, comprising absorption maxima at $\lambda_1$=223 nm ($\epsilon$=73600, log $\epsilon$=4.87) and $\lambda_2$=270 nm ($\epsilon$=17700, log $\epsilon$=4.25);
     c. infrared absorption spectrum shown in FIG. 2, comprising absorption maxima at 3309 and 1669 (br) cm$^{-1}$ (KBr disc);
     d. proton magnetic resonance spectrum shown in FIG. 3 (400 MHz, d$_6$-DMSO, 55° C.; referenced to CD$_3$SOCD$_2$H quintet at 2.50 ppm);
     e. carbon-13 nuclear magnetic resonance signals comprising the following chemical shifts (in ppm, referenced to CD$_3$SOCD$_2$H heptet at 39.5 ppm, 55° C.), multiplicities (as the number of attached protons), chemical shifts of attached protons, and the COSY correlation of attached protons of select carbons:

| *Residue | $^{13}$C (ppm, multiplicity) | 1H (ppm) | COSY (ppm) |
| --- | --- | --- | --- |
| #Trp | 120.8 (CH) | 7.05 | 7.34 |
| Trp | 126.0 (CH) | 7.19 | 10.89 |
| #Trp | 120.8 (CH) | 7.05 | 7.54 |
| Trp | 117.2 (CH) | 7.54 | 7.05 |
| Trp | 112.8 (CH) | 7.34 | 7.05 |
| Trp | N—H | 10.89 | 7.19 |
| DHB | 126.3 (CH) | 6.21 | 1.72 |
| DHB | 13.0 (CH3) | 1.72 | 6.21 |
| DHA | 103.7 (CH2) | 5.98 | |
| | | 5.40 | |
| AviCys | 130.2 (CH) | 6.83 | 8.38, 5.46 |
| AviCys | 102.5 (CH) | 5.46 | 6.83 |
| AviCys | N—H | 8.38 | 6.83 |

*Trp = tryptophan; DHB = dehydrobutyrine; DHA = dehydroalanine; AviCys = aminovinyl cysteine.
Signals overlapped      f. retention time of 9.1 minutes when chromatographed under the following conditions:
       Column: 15.0×0.46 cm PLRPs (Polymer Labs, 5 um)
       Flow rate: 1 ml/min
       Detection: 254 nm
       Eluant: acetonitrile (Solvent A) 0.05% Formic Acid in Water (pH 2.83) (solvent B)

Protocol: the following solvent ratios and gradient:

| Time | Solvent mixture A/B, v/v |
|---|---|
| 0 min | 25/75 |
| 2 min | 25/75 |
| 10 min | 38/62 |
| 20 min | 38/62. |

Figure 4:
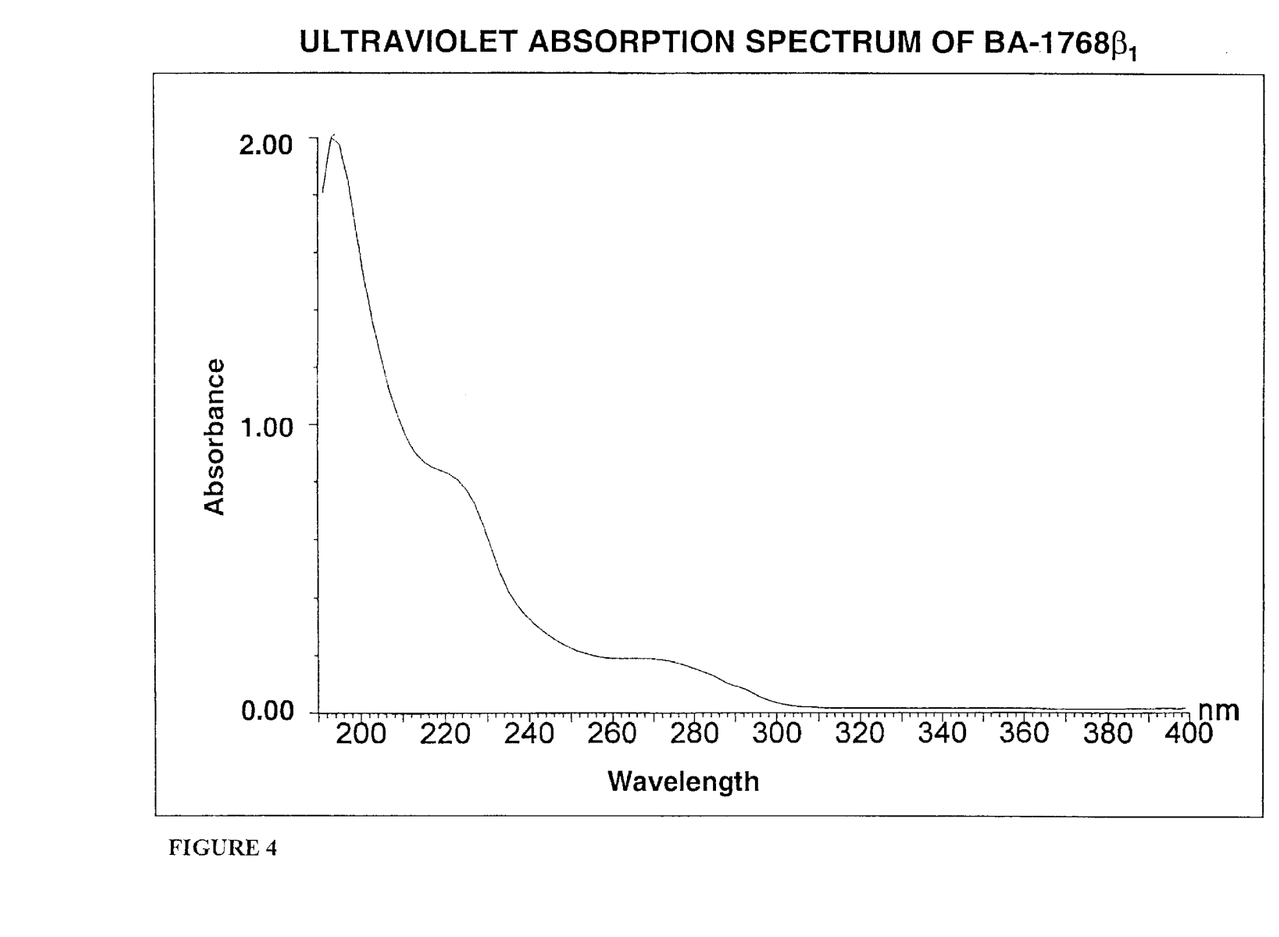
FIG. 4 is the ultraviolet absorption spectrum of MF-BA-1768$\beta_1$ (0.025 µg/ml solution in 35% acetonitrile-0.05% formic acid in water, pH 2.83).

6. A composition comprising:

a therapeutically effective amount of compound MF-BA-1768$\beta_1$ or a pharmaceutically acceptable salt thereof; and, a pharmaceutically acceptable carrier, wherein compound MF-BA-1768$\beta_1$ has the following physicochemical characteristics:

a. molecular weight: 2180.805, calculated monoisotopic mass from $[M+2H]^{2+}$ at m/z 1091.410, determined by high resolution ESI-FTMS using reference compound peptide mellitin ($3^+$ charge);

b. ultraviolet spectrum shown in FIG. 4, comprising absorption maxima at $\lambda_1$ 221 nm ($\epsilon$=105300, log $\epsilon$=5.02) and $\lambda_2$ 270 nm ($\epsilon$=19300, log $\epsilon$=4.28);

c. infrared absorption spectrum shown in FIG. 5, comprising absorption maxima at 3309 and 1669 cm$^{-1}$ (KBr disc);

d. proton magnetic resonance spectrum shown in FIG. 6 (400 MHz, d$_6$-dmso, 55° C.; referenced to CD$_3$SOCD$_2$H quintet at 2.50 ppm);

e. carbon-13 nuclear magnetic resonance signals comprising the following chemical shifts (in ppm, referenced to CD$_3$SOCD$_2$H heptet at 39.5 ppm, 55° C.), multiplicities (as the number of attached protons), chemical shifts of attached protons, and COSY correlation of the attached protons of select carbons:

| *Residue | 13C (ppm, multiplicity) | 1H (ppm) | COSY (ppm) |
|---|---|---|---|
| Trp | 120.9 (CH) | 7.06 | 7.32 |
| Trp | 128.0 (CH) | 7.12 | 10.71 |
| Trp | 118.2 (CH) | 6.97 | 7.51 |
| Trp | 117.8 (CH) | 7.51 | 6.97 |
| Trp | 111.2 (CH) | 7.32 | 7.06 |
| Trp | N—H | 10.71 | 7.12 |
| DHB | 125.7 (CH) | 6.21 | 1.70 |
| DHB | 12.6 (CH3) | 1.70 | 6.21 |
| DHA | 103.0 (CH2) | 6.04 | |
| | | 5.39 | |
| AviCys | 130.1 (CH) | 6.83 | 8.35, 5.45 |
| AviCys | 102.1 (CH) | 5.45 | 6.83 |
| AviCys | N—H | 8.35 | 6.83 |

*Trp = tryptophan; DHB = dehydrobutyrine; DHA = dehydroalanine; AviCys = aminovinyl cysteine.

f. retention time ($R_t$) of 10.6 minutes when chromatographed under the following conditions:
Column: 15.0×0.46 cm PLRPs (Polymer Labs, 5 um)
Flow rate: 1 ml/min
Detection: 254 nm
Eluant: acetonitrile (Solvent A) 0.05% Formic Acid in Water (pH 2.83) (solvent B)

Protocol: the following solvent ratios and gradient:

| Time | Solvent mixture A/B, v/v |
|---|---|
| 0 min | 25/75 |
| 2 min | 25/75 |
| 10 min | 38/62 |
| 20 min | 38/62. |

7. A method for treating a bacterial infection comprising administering to a patient in need thereof a therapeutically effective amount of compound MF-BA-1768$\alpha_1$ which has the following physicochemical characteristics:

a. molecular weight: 2214.880, calculated monoisotopic mass from $[M+2H]^{2+}$ at m/z 1108.449, determined by high resolution ESI-FTMS using reference compound peptide mellitin ($3^+$ charge);

b. ultraviolet absorption spectrum shown in FIG. 1, comprising absorption maxima at $\lambda_1$=223 nm ($\epsilon$=73600, log $\epsilon$=4.87) and $\lambda_2$=270 nm ($\epsilon$=17700, log $\epsilon$=4.25);

c. infrared absorption spectrum shown in FIG. 2, comprising absorption maxima at 3309 and 1669 (br) cm$^{-1}$, (KBr disc);

d. proton magnetic resonance spectrum shown in FIG. 3 (400 MHz, d$_6$-DMSO, 55° C.; referenced to CD$_3$SOCD$_2$H quintet at 2.50 ppm);

e. carbon-13 nuclear magnetic resonance signals comprising the following chemical shifts (in ppm, referenced to CD$_3$SOCD$_2$H heptet at 39.5 ppm, 55° C.), multiplicities (as the number of attached protons), chemical shifts of attached protons, and the COSY correlation of attached protons of select carbons:

| *Residue | 13C (ppm, multiplicity) | 1H (ppm) | COSY (ppm) |
|---|---|---|---|
| #Trp | 120.8 (CH) | 7.05 | 7.34 |
| Trp | 126.0 (CH) | 7.19 | 10.89 |
| #Trp | 120.8 (CH) | 7.05 | 7.54 |
| Trp | 117.2 (CH) | 7.54 | 7.05 |
| Trp | 112.8 (CH) | 7.34 | 7.05 |
| Trp | N—H | 10.89 | 7.19 |
| DHB | 126.3 (CH) | 6.21 | 1.72 |
| DHB | 13.0 (CH3) | 1.72 | 6.21 |
| DHA | 103.7 (CH2) | 5.98 | |
| | | 5.40 | |
| AviCys | 130.2 (CH) | 6.83 | 8.38, 5.46 |
| AviCys | 102.5 (CH) | 5.46 | 6.83 |
| AviCys | N—H | 8.38 | 6.83 |

*Trp = tryptophan; DHB = dehydrobutyrine; DHA = dehydroalanine; AviCys = aminovinyl cysteine.
Signals overlapped f. retention time of 9.1 minutes when chromatographed under the following conditions:
Column: 15.0×0.46 cm PLRPs (Polymer Labs, 5 um)
Flow rate: 1 ml/min
Detection: 254 nm
Eluant: acetonitrile (Solvent A) 0.05% Formic Acid in Water (pH 2.83) (solvent B)

Protocol: the following solvent ratios and gradient:

| Time | Solvent mixture A/B, v/v |
|---|---|
| 0 min | 25/75 |
| 2 min | 25/75 |
| 10 min | 38/62 |
| 20 min | 38/62. |

8. A method for treating a bacterial infection comprising administering to a patient in need thereof a therapeutically effective amount of compound MF-BA-1768$\beta_1$ which has the following physicochemical characteristics:

a. molecular weight: 2180.805, calculated monoisotopic mass from $[M+2H]^{2+}$ at m/z 1091.410, determined by high resolution ESI-FTMS using reference compound peptide mellitin ($3^+$ charge);

b. ultraviolet spectrum shown in FIG. 4, comprising absorption maxima at $\lambda_1$ 221 nm ($\epsilon$=105300, log $\epsilon$=5.02) and $\lambda_2$ 270 nm ($\epsilon$=19300, log $\epsilon$=4.28);

c. infrared absorption spectrum shown in FIG. 5, comprising absorption maxima at 3309 and 1669 cm$^{-1}$ (KBr disc);

d. proton magnetic resonance spectrum shown in FIG. 6 (400 MHz, $d_6$-dmso, 55° C.; referenced to $CD_3SOCD_2H$ quintet at 2.50 ppm);

e. carbon-13 nuclear magnetic resonance signals comprising the following chemical shifts (in ppm, referenced to $CD_3SOCD_2H$ heptet at 39.5 ppm, 55° C.), multiplicities (as the number of attached protons), chemical shifts of attached protons, and COSY correlation of the attached protons of select carbons:

| *Residue | 13C (ppm, multiplicity) | 1H (ppm) | COSY (ppm) |
|---|---|---|---|
| Trp | 120.9 (CH) | 7.06 | 7.32 |
| Trp | 128.0 (CH) | 7.12 | 10.71 |
| Trp | 118.2 (CH) | 6.97 | 7.51 |
| Trp | 117.8 (CH) | 7.51 | 6.97 |
| Trp | 111.2 (CH) | 7.32 | 7.06 |
| Trp | N—H | 10.71 | 7.12 |
| DHB | 125.7 (CH) | 6.21 | 1.70 |
| DHB | 12.6 (CH3) | 1.70 | 6.21 |
| DHA | 103.0 (CH2) | 6.04 5.39 | |
| AviCys | 130.1 (CH) | 6.83 | 8.35, 5.45 |
| AviCys | 102.1 (CH) | 5.45 | 6.83 |
| AviCys | N—H | 8.35 | 6.83 |

*Trp = tryptophan; DHB = dehydrobutyrine; DHA = dehydroalanine; AviCys = aminovinyl cysteine.

f. retention time ($R_t$) of 10.6 minutes when chromatographed under the following conditions:
Column: 15.0×0.46 cm PLRPs (Polymer Labs, 5 um)
Flow rate: 1 ml/min
Detection: 254 nm
Eluant: acetonitrile (Solvent A) 0.05% Formic Acid in Water (pH 2.83) (solvent B)
Protocol: the following solvent ratios and gradient:

| Time | Solvent mixture A/B, v/v |
|---|---|
| 0 min | 25/75 |
| 2 min | 25/75 |
| 10 min | 38/62 |
| 20 min | 38/62. |

9. The method of either claim 7 or claim 8, wherein the bacterial infection is caused by Staphylococcus, Enterococcus, Streptococcus, Haemophilus or Escherichia species bacteria.

10. The method of claim 9, wherein the bacterial species is selected from the group consisting of *Staphylococcus aureus, Staphylococcus epidermis, Staphylococcus haemolyticus, Enterococcus faecalis, Enterococcus faecium, Streptococcus pneumoniae, Streptococcus pyrogenes, Haemophilus influenzae* and *Eschericia coli*.

\* \* \* \* \*